United States Patent [19]

Okubo

[11] Patent Number: 5,092,008
[45] Date of Patent: Mar. 3, 1992

[54] ABSORBENT SHEET LIKE MAT

[75] Inventor: Takemi Okubo, Fukuoka, Japan

[73] Assignee: Esu-Oh Giken Co., Ltd., Fukuoka, Japan

[21] Appl. No.: 460,083

[22] PCT Filed: Apr. 6, 1989

[86] PCT No.: PCT/JP89/00371
§ 371 Date: Dec. 6, 1989
§ 102(e) Date: Dec. 6, 1989

[87] PCT Pub. No.: WO89/09560
PCT Pub. Date: Oct. 19, 1989

[30] Foreign Application Priority Data

Apr. 7, 1988 [JP] Japan .................. 63-47474[U]

[51] Int. Cl.⁵ ............................................. A47G 9/00
[52] U.S. Cl. ........................................ 5/484; 5/485; 604/367
[58] Field of Search ............... 604/367, 359, 375; 5/484, 502, 485, 482, 487

[56] References Cited

U.S. PATENT DOCUMENTS

| | | | |
|---|---|---|---|
| 2,350,363 | 6/1944 | Massa | 5/502 |
| 2,707,289 | 5/1955 | Taggart | 5/484 |
| 3,137,871 | 6/1964 | Florio | 5/502 |
| 3,871,037 | 3/1975 | Willington | 5/484 |
| 3,989,867 | 11/1976 | Sisson | 5/484 |
| 4,340,556 | 7/1982 | Ciencewicki | 604/375 |
| 4,354,487 | 10/1982 | Olzkowski | 604/357 |
| 4,392,861 | 7/1983 | Butterworth | 604/375 |
| 4,445,242 | 5/1984 | Bowen | 5/485 |
| 4,599,756 | 7/1986 | Koffler | 5/485 |
| 4,755,178 | 7/1988 | Insley | 604/367 |
| 4,826,497 | 5/1989 | Marcus | 604/359 |
| 4,839,934 | 6/1989 | Rojas | 5/502 |
| 4,853,086 | 5/1989 | Graef | 604/375 |
| 4,882,204 | 11/1989 | Tenenbaum | 604/367 |

FOREIGN PATENT DOCUMENTS

| | | |
|---|---|---|
| 51-33914 | 3/1976 | Japan . |
| 53-66893 | 6/1978 | Japan . |
| 53-129515 | 10/1978 | Japan . |
| 54-72399 | 5/1979 | Japan . |
| 56-5519 | 1/1981 | Japan . |
| 5993258 | 6/1984 | Japan . |

Primary Examiner—Gary L. Smith
Assistant Examiner—F. Saether
Attorney, Agent, or Firm—Michael N. Meller

[57] ABSTRACT

A sheet-like mat capable of providing a comfortable resting environment by adsorbing sweat emitted from a body of a user or moisture in underwear, bedding or the like. This sheet-like mat can be obtained by dividing an inside of a mat cover into a plurality of bag-like spaces and arranging a bag-packed drying agent in each bag-like space, respectively. A drying agent sheet may be used in place of the bag packed drying agent.

2 Claims, 5 Drawing Sheets

ABSORBENT SHEET LIKE MAT

TECHNICAL FIELD

The present invention relates to a sheet-like mat. More particularly, it relates to a sheet-like mat used independently as a bedding such as a sleeping mat, a quilt, a cushion, a bed for a sick person or the like, or used with a cover such as a bed sheet or the like and capable of providing a comfortable resting environment by absorbing sweat emitted from a body of a user or a moisture in underwear, bedding or the like.

BACKGROUND ART

A bed sheet made of a woven fabric or a knitted fabric of a cotton fiber of the above kind of mat is known. Since cotton fiber has a superior hygroscopicity and water absorption, the cotton fiber can absorb sweat, moisture, blood or the like, to thereby prevent a sticky feeling due to sweat or the like.

However, even if the bed sheet is made of a cotton fiber or the like having superior water absorption properties, a water content which the bed sheet of the woven fabric or the knitted fabric can absorb is relatively low and the fabric is quickly saturated with the water. Therefore, in particular when bedding is used during hot weather, or is continuously used for a long term by a sick person, a problem arises in that the conventional bed sheet of cotton fiber or the like cannot sufficiently absorb the generated water content. Further, another problem arises in that a smell stemming from sweat, blood, water emitted from a human body or the like cannot be removed until the material is washed.

DISCLOSURE OF THE INVENTION

An object of the present invention is to solve the above-mentioned problems of the prior art and to provide a sheet-like mat having a high water-absorbing ability and capable of maintaining a comfortable and dry environment without a stuffy condition caused by sweat and moisture, and less likely to cause bedsores, and if necessary, capable of eliminating bad smells.

The object of the present invention is achieved by a sheet-like mat comprised of a mat cover the inside of which is divided into a plurality of bag-like spaces, and a drying agent packed into a bag and contained in the bag-like spaces in such a manner that the drying agent cannot fall out of the bag-like spaces.

Since the drying agent is contained inside the sheet-like mat in accordance with the present invention, it is possible to provide a comfortable sleeping environment and prolong the bedding life, by absorbing a water content and moisture due to the sweat, blood, urine or the like in the bedding to maintain surfaces of the bedding, underwear or the human skin in a dry condition by suitably selecting a quantity of the drying agent.

It is possible to absorb the smell of sweat, blood or water emitted from the human body by adding a deodorant to the drying agent.

A magnesium sulfate, a high polymer absorbent, a silica gel or the like can be used as the drying agent.

When the magnesium sulfate $MgSO_4 \cdot nH_2O$, wherein $0 \leq n < 5$, is used, it is possible to obtain a strong drying power, i.e., a strong water absorbing power, compared with silica gel, and a superior effect without a deliquescence. There is little danger of harm when magnesium sulfate is orally inhaled, and the magnesium sulfate can be regenerated, which are advantages obtained by the use of magnesium sulfate.

An activated alumina, a zeolite or an activated charcoal can be used as the deodorant.

When dividing the inside of the mat cover into a plurality of spaces and using the drying agent packed into bags, it is possible to change or regenerate the bags containing the drying agent.

More particularly, when a circumferential edge enclosing bag spaces of the mat cover can be freely opened and closed, insertion and removal of the drying agent are rapidly and easily accomplished.

When increasing the water absorption properties of a covering material of a front side, i.e., an upper side, of the mat cover, and reducing the water absorption properties of a back side, i.e., a lower side, of the mat cover, or using a back side material which is a nonwater absorption, water proof or a nonair permeable material, or using a material at a bottom side surface of a bag in which the drying agent is included which is nonabsorbent, nonwater permeable or nonair permeable, it is possible to absorb a high content of water from underwear, the quilt or the human body, to limit unnecessary water absorption from a floor and a base portion of the bed, to effectively utilize an absorption power of the drying agent, and to maintain the absorption power for a long term.

Further, the object of the present invention can be attained by a sheet-like material comprising a mat cover having a bag-like shape and a drying agent sheet contained in the mat cover, wherein the drying agent sheet is manufactured by impregnating a sheet material such as a paper, a fabric or the like with a water solution containing a drying agent, and then removing the water content thereof.

The latter sheet-like mat is different from the former sheet-like mat in that, in the latter sheet-like mat, the sheet-like drying agent is used in place of the drying agent packed into bags in the former sheet-like mat, and accordingly, it is possible to arrange the sheet-like drying agent inside the sheet-like mat without dividing the mat cover into a plurality of bag-like spaces. In this sheet-like mat, it is preferable to arrange the drying agent sheet so that it can be to removed from the mat cover, or to make different portions of the mat cover of materials having different water absorption properties.

BEST MODE OF CARRYING OUT THE INVENTION

The present invention will be explained on the basis of several embodiments with reference to the accompanying drawings.

First Embodiment

Figure 1:
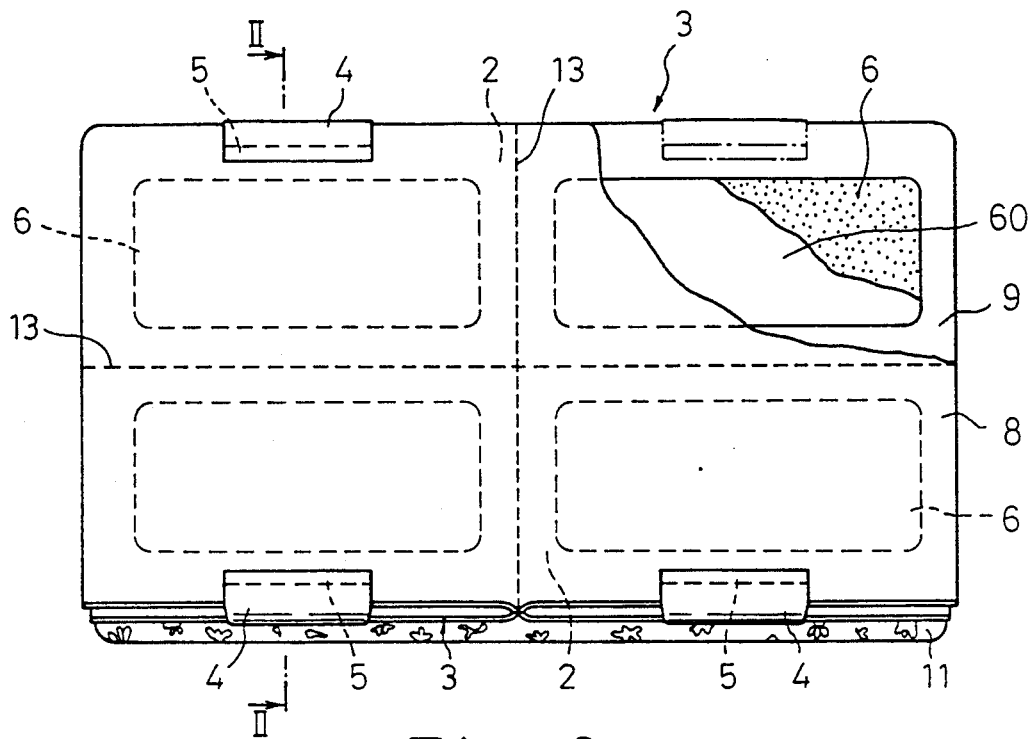
FIG. 1 is a partially cutaway schematic perspective view of an preferable embodiment, i.e., a first embodiment of the sheet-like mat in accordance with the present invention.
Figure 2:
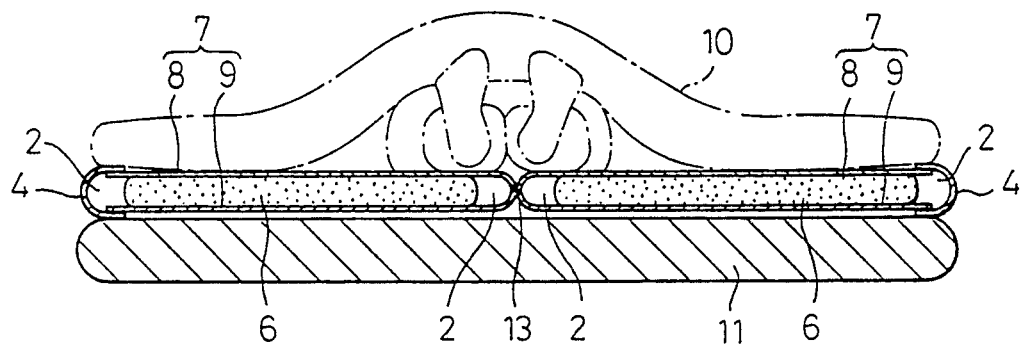
FIG. 2 is a transverse sectional view taken along the line II—II of FIG. 1.
Figure 3:
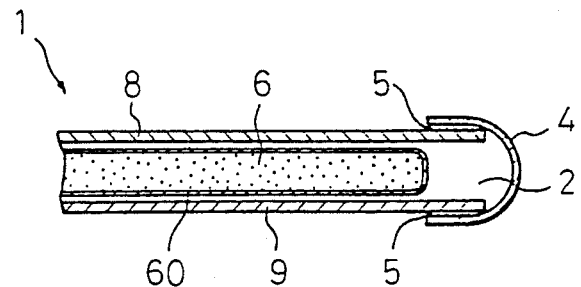
FIG. 3 is a partial sectional view illustrating a state in which a circumferential edge of the mat cover is closed by a fastener having a sheet-like shape.

In a sheet-like mat 1 of a first embodiment illustrated in FIGS. 1 to 3, a bag-like space 2 of a mat cover 7 is divided by a sewing thread 13 to form four spaces, a circumferential edge 3 thereof can be freely opened or closed by a sheet-like fastener 5 provided on a holding cloth 4. Further, an upper side fabric or a front side fabric 8 in the mat cover 7 of the sheet-like mat 1 is made of a cotton fiber fabric having superior water absorption properties and an air permeability, and a lower side fabric or a back side fabric 9 is made of a nonwoven fabric having a moisture proofness, so that the upper side of the mat cover is able to easily absorb water and the lower side fabric of the mat cover cannot easily absorb water.

A drying agent 6 is contained in a flat bag body 60 made of a polyester nonwoven fabric having a water permeability and an air permeability.

A magnesium sulfate anhydride is used as the drying agent 6, and an activated alumina of about 10 weight% of the drying agent 6 is blended therein. The drying agent is enclosed in a thin layer of 200 g/m² in a flat bag body. In this embodiment, sweat and moisture emitted from a human body, underwear and a quilt 10 are absorbed through the upper side fabric 8 of the mat cover 7 into the strong drying agent 6 of the magnesium sulfate packed into the bag spaces, and thus a surface of the human body, underwear and the quilt are kept dry, to provide a comfortable sleeping environment. In this case, moisture rising from a floor, a bed or a sleeping mat 11 and moisture in the atmosphere is not easily absorbed by the lower side fabric, and therefore, the water absorbing power of the drying agent is not reduced by an unnecessary water absorption from the under side. Further, the deodorant of the activated alumina in the drying agent 6 removes the smell of sweat, urine, body fluids or fungi, to provide a more comfortable sleeping environment.

A deliquescent phenomenon caused by an increase of the water absorption as appearing in silica gel or the like does not appear in the magnesium sulfate anhydrate used as the drying agent 6, and accordingly the magnesium sulfate anhydrate can be safely used over a long term. Further, even if the magnesium sulfate anhydrate is orally inhaled by a person, no harm results.

When a water quantity absorbed into the drying agent is increased, and thus a water-absorbing ability of the drying agent is reduced, it is possible to remove the holding fabric 4 from the fastener 5, take out the bag body 60 of the drying agent 6, and exchange the used drying agent 6 for a new drying agent or a regenerated drying agent 6.

Further, when the sheet-like mat is not in use, it is possible to store the mat in a state in which the mat cover 7 and the long body 60 of the drying agent are stored separately.

Second Embodiment

Figure 4:
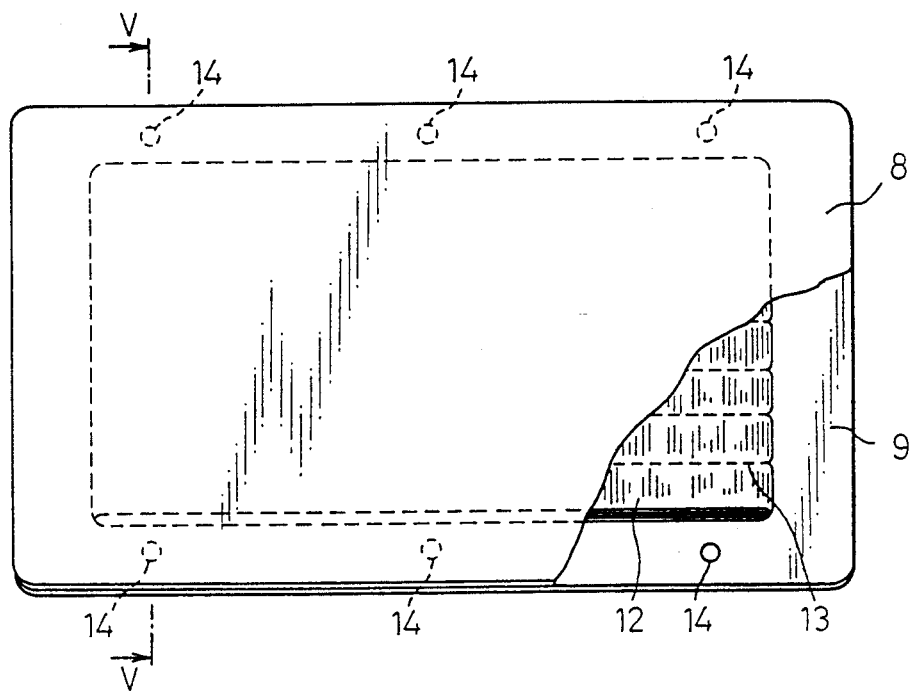
FIG. 4 is a partially cutaway schematic perspective view of another preferable embodiment, i.e., a second embodiment of the sheet-like mat in accordance with the present invention.
Figure 5:
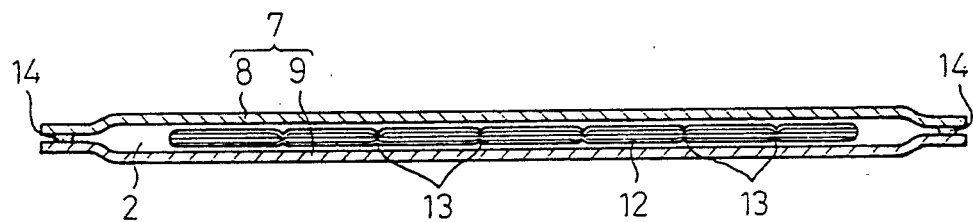
FIG. 5 is a transverse sectional view taken along the line V—V of FIG. 4.

A sheet-like mat of the second embodiment illustrated in FIGS. 4 and 5 is an example of the sheet-like mat in which a drying agent sheet 12 is manufactured by impregnating it with a water solution containing a drying agent, i.e., magnesium sulfate is impregnated into a reinforced Japanese paper, the paper is dried, and a plurality of sheets of the Japanese paper are sewn by a sewing thread 13. The sheet 12 is contained in the mat cover 7. Further, this embodiment is an example in which a cotton woven fabric having good water absorption properties is used as an upper side fabric of the mat cover 7 and a nonwoven fabric having a moisture proofness is used as a lower side fabric. In the same manner as in the first embodiment, in the second embodiment, unnecessary water absorption by the lower side can be prevented and a strong water absorbing force and a long-term water absorption can be maintained, so that a good mat environment can be provided. Further, a side circumferential edge of the mat cover 7 is held in a freely operable or closable state by hooks 14, and accordingly, it is possible to easily exchange, or insert or remove, the drying agent sheet.

Third Embodiment

Figure 6:
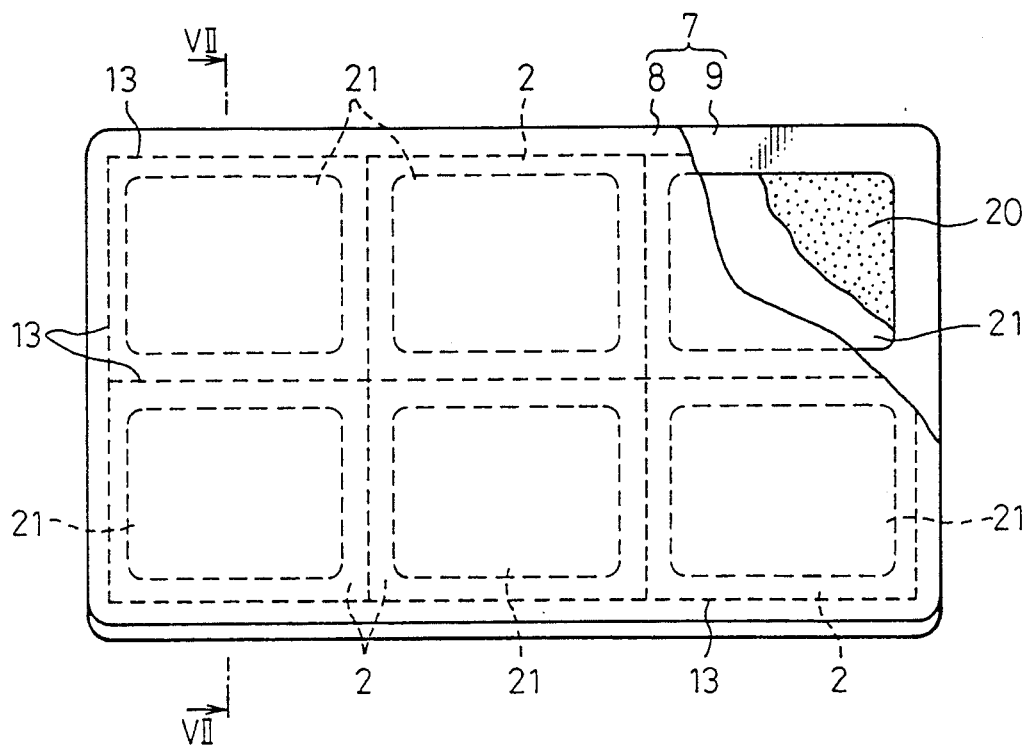
FIG. 6 is a partially cutaway schematic perspective view of another preferable embodiment, i.e., a third embodiment of the sheet-like mat in accordance with the present invention.
Figure 7:
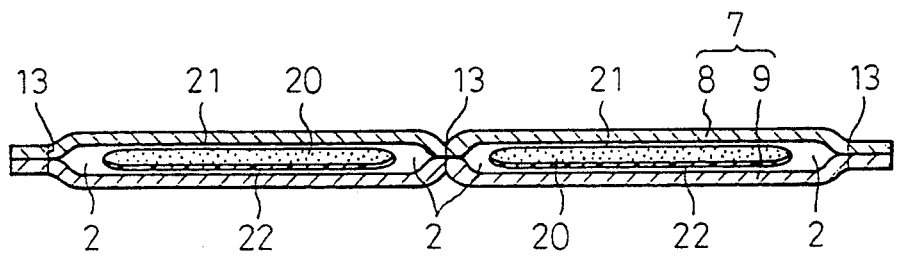
FIG. 7 is a transverse sectional view taken along the line VII—VII of FIG. 6.

A sheet-like mat of the third embodiment illustrated in FIGS. 6 and 7 is an example of a sheet-like mat in which a mat cover 7 is a nonwoven fabric having water absorption properties and is divided into six bag-like spaces 2 by a sewing thread 13.

A powder-like chemical substance 20, in which a drying agent of a magnesium sulfate anhydride and a deodorant of an activated alumina are blended at a weight ratio of 3 to 1, is packed in a layer-like state at a rate of 250 g/m² into a flat bag body 21 of a nonwoven fabric having water absorption properties. Further, a plastic film 22 having a water proofness is coated on a surface of a bottom side wall of the flat bag body to provide a water proofness thereto. A sheet-like bag body 21 in which the chemical substance is packed is accommodated in the bag-like spaces 2 of the mat cover 7.

In this embodiment, sweat and moisture of the human body and the bedding are absorbed through the mat cover 7 of the nonwoven fabric having water absorption properties and an upper side of the sheet-like bag body 21 into the drying agent in the same manner as in the former embodiments. Water absorption from the under side is limited, because the bottom side of the sheet-like bag body 21 is coated with a waterproof plastic film.

Further, a smell of sweat, urine, blood or the like can be simultaneously deodorized by an activated alumina having a strong deodorizing power. Reuse of the sheet-like mat can be obtained by regenerating the drying agent and the deodorant by folding the used mat sheet which has absorbed much water, and putting the mat into an electronic oven, whereby the mat cover 7 and the bag body 21 are dehydrated.

Fourth Embodiment

Figure 8A:
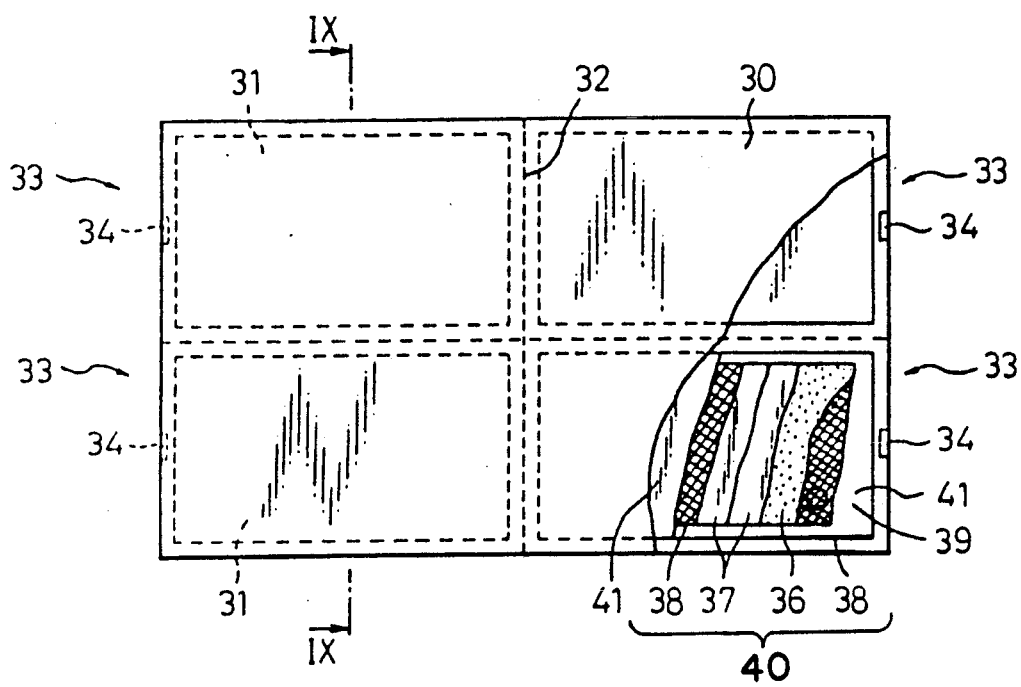
FIG. 8 is a partially cutaway schematic plan view of still another preferable embodiment of the sheet-like mat in accordance with the present invention.
FIG. 8B is a plan view illustrating a concave and convex lattice pattern shown in a circle 42 of FIG. 8A.
Figure 8B:
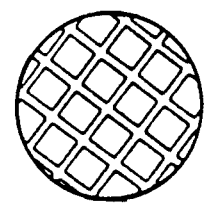
Figure 9:
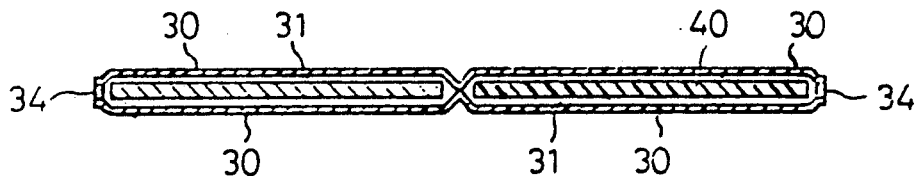
FIG. 9 is a transverse sectional view taken along the line IX—IX of FIG. 8.
Figure 10:
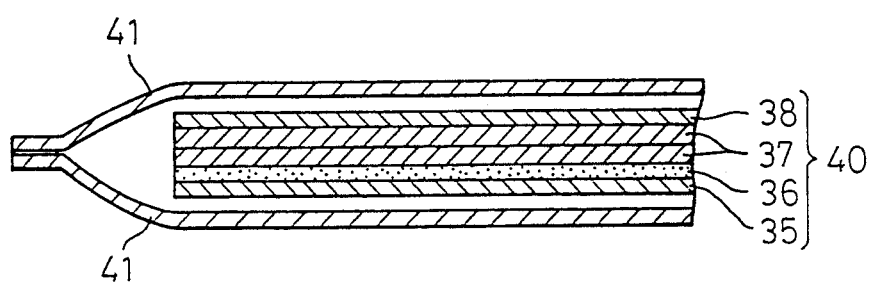
FIG. 10 is an enlarged sectional view illustrating a composition of a drying sheet.

A sheet-like mat of the fourth embodiment illustrated in FIGS. 8 to 10 uses a mat cover having a dimension of 86 cm × 56 cm and made of a blended yarn of a polyester of 65% and a cotton of 35%; the mat cover is sewn by a sewing thread 32 so that four rectangle bag-like spaces are formed, outer circumferential edges 33 opposite to each other on the short sides of the mat cover are opened, and sheet-like fasteners 34 are fixed in opposing positions inside the opened outer circumferential edges. A drying agent sheet 40 is made of a powder-like chemical substance 36 in which a drying agent of a magnesium sulfate anhydride and a deodorant of an activated alumina are blended at a weight ratio of 1 to 1 and laid in a layered state at a rate of about 200 g/m$^2$ on a paper sheet 35 of a pulp group having water adsorption properties and air permeability, two extremely thin sheets of polyester synthetic paper 37 having a weight per unit area of 200 g/m$^2$ and the pulp group paper sheet 38 are sequentially plied thereon, and then the piled materials are formed as one body by pressing in such a manner that a concave and convey lattice pattern is formed. The drying agent sheet 40 is illustrated in greater detail by the enlarged drawing of FIG. 10 showing the layers of the sheet. This drying agent sheet 40 is enclosed in a flat bag body 41 of a polyester nonwoven fabric having an air permeability, a water permeability, and a unit area weight of 40 g/m$^2$, and a circumference of the flat bag body 41 is sealed by heat sealing. The flat bag bodies 41 enclosing the drying agent sheets 40 are inserted from the openings 33 of the mat cover 30 into the bag-like spaces 31 of the mat cover 30, respectively, and the sheet-like bag bodies 41 are held in the bag-like spaces by pressing together the opposing sheet-like fasteners 34 above and below, to join the two sheet-like fasteners 34 to each other. In this embodiment, sweat and moisture are absorbed through the mat cover 30 having the air permeability and the water permeability, the sheet-like bag body 41 made of the polyester, the pulp group paper sheets 35 and 38, and the polyester synthetic paper 37 into the chemical substance 36 included in the drying agent, and then the bedding and the human body are kept dry in the same manner as in the third embodiment. Further, the smell of sweat, urine or the like can be simultaneously deodorized by the chemical substance 36 including the deodorant, and a comfortable bedding environment and longer bed life can be obtained. Further, when the chemical substance 36 absorbs enough water and becomes saturated, the flat bag body 41 may be exchanged for a new flat bag body by separating the sheet like fastener 34 and removing the flat bag body 41 from the mat cover 30. The removed used flat bag body 41 can be regenerated by heating the flat bag body 41, in which the drying agent sheet is enclosed, in an electronic oven. The regeneration of the drying agent sheet can be performed by folding the wet sheet-like mat in which the flat bag body 41 is enclosed and heating the sheet-like mat in the electronic oven.

INDUSTRIAL APPLICABILITY

Since the sheet-like mat in accordance with the present invention includes a drying agent therein, the sheet-like mat can absorb sweat, urine, blood or moisture in underwear, and thus the bedding or the human body are kept dry, a comfortable bedding environment which is not sticky and less likely to cause bed sore can be obtained, and thus the sheet-like mat in accordance with the present invention guarantees a comfortable sleeping environment for healthy people and an easing of pains for the sick.

I claim:

1. A sheet-like mat comprising a bag-like mat cover having a substantially rectangular shape sewn by a sewing thread so that four substantially rectangular bag-like spaces having a corner of the bag-like mat cover are formed, respectively, and four drying agent sheet units included in each rectangular bag-like space, and said drying agent sheet unit comprised of a flat bag body of a nonwoven fabric having an air permeability and a water permeability and a drying agent sheet piled body constituted by sequentially piling a paper sheet having water absorption properties and air permeability, a powder-like chemical substance in which a drying agent of a magnesium sulfate anhydride and a deodorant of an activated alumina are blended and laid on said paper sheet, two synthetic papers and a paper sheet having water absorption properties and air permeability and applying an embossed pattern to form one body and enclosed in said flat bag body, and further an outer circumferential portion of each rectangular bag-like space of the bag-like mat cover is provided with a closing means capable of being opened or closed.

2. A sheet-like mat according to claim 1, wherein a material having higher absorption properties compared with that of a covering material on a backside of the bag-like mat cover is used as a covering material on a front side of the bag-like mat cover.

* * * * *